(12) United States Patent
Schultz et al.

(10) Patent No.: US 10,556,857 B2
(45) Date of Patent: Feb. 11, 2020

(54) HYDRAZIDE COMPOUNDS SUITABLE FOR NUCLEATING POLYLACTIC ACID POLYMER

(71) Applicant: 3M INNOVATIVE PROPERTIES COMPANY, St. Paul, MN (US)

(72) Inventors: Nathan E. Schultz, Woodbury, MN (US); Liming Song, Woodbury, MN (US); Fuming B. Li, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 66 days.

(21) Appl. No.: 15/737,473

(22) PCT Filed: Jun. 14, 2016

(86) PCT No.: PCT/US2016/037361
§ 371 (c)(1),
(2) Date: Dec. 18, 2017

(87) PCT Pub. No.: WO2016/209663
PCT Pub. Date: Dec. 29, 2016

(65) Prior Publication Data
US 2018/0186728 A1   Jul. 5, 2018

Related U.S. Application Data

(60) Provisional application No. 62/182,821, filed on Jun. 22, 2015.

(51) Int. Cl.
| | | |
|---|---|---|
| C07C 243/00 | (2006.01) | |
| C07C 243/28 | (2006.01) | |
| C08K 5/25 | (2006.01) | |

(52) U.S. Cl.
CPC .............. *C07C 243/28* (2013.01); *C08K 5/25* (2013.01)

(58) Field of Classification Search
None
See application file for complete search history.

(56) References Cited

U.S. PATENT DOCUMENTS

| 3,734,885 | A | * | 5/1973 | Muller et al. ............ C08K 5/25 |
|---|---|---|---|---|
| | | | | 524/100 |
| 6,005,068 | A | | 12/1999 | Gruber |
| 6,111,060 | A | | 8/2000 | Gruber |
| 7,034,102 | B2 | | 4/2006 | Tobita |
| 7,910,643 | B2 | | 3/2011 | Tobita |
| 2004/0214983 | A1 | | 10/2004 | Tobita |
| 2016/0272789 | A1 | | 9/2016 | Pfaendner |

FOREIGN PATENT DOCUMENTS

| CN | 1094394 | 11/1994 |
|---|---|---|
| DE | 102012022482 | 5/2014 |
| EP | 1676887 | 7/2006 |
| EP | 1795560 | 6/2007 |

OTHER PUBLICATIONS

NatureWorks Product Guide 2017, p. 1-7 2017.*
"Ingeo Biopolymer 6100D Technical Data Sheet", NatureWorks, [on line], [retrieved from internet on Jan. 22, 2018], URL <https://www.natureworksllc.com/~/media/Files/NatureWorks/Technical-Documents/Technical-Data-Sheets/TechnicalDataSheet_6100D_fiber-melt-spinning_pdf.pdf>, 4pgs.
"Ingeo Biopolymer 6202D Technical Data Sheet", NatureWorks LLC, [on line], [retrieved from internet on Jan. 22, 2018], URL <https://www.natureworksllc.com/~/media/Files/NatureWorks/Technical-Documents/Technical-Data-Sheets/TechnicalDataSheet_6202D_fiber-melt-spinning_pdf.pdf>, 4pgs.
Al-Itry, "Biopolymer Blends Based on Poly (Lactic Acid): Shear and Elongation Rheology/Structure/Blowing Process Relationships", Polymers, May 2015, vol. 7, pp. 939-962, XP055295352.
Garlotta, "A Literature Review of Poly(Lactic Acid)", Journal of Polymers and the Environment, Apr. 2001, vol. 9, No. 2, pp. 63-84.
Kawamoto, "Nucleating Agent for Poly(L-Lactic Acid)—An Optimization of Chemical Structure of Hydrazide Compound for Advanced Nucleation Ability", Journal of Applied Polymer Science, 2007, vol. 103, pp. 198-203.
Qi, "Effect of Aliphatic Diacyl Adipic Dihydrazides on the Crystallization of Poly(Lactic Acid)", Journal of Applied Polymer Science, 2015, vol. 132, No. 23, pp. 1-8, XP55295289.
International Search Report for PCT International Application No. PCT/US2016/037361, dated Aug. 25, 2016, 5pgs.

* cited by examiner

*Primary Examiner* — Robert T Butcher

(74) *Attorney, Agent, or Firm* — Carolyn A. Fischer

(57) ABSTRACT

Presently describes are hydrazide (e.g. dihydrazide) compounds suitable for use as a nucleating agent for a polylactic acid ("PLA") polymer. Also described are articles such as a film or fiber comprising the semicrystalline polylactic acid polymer and a nucleating agent.

13 Claims, No Drawings

HYDRAZIDE COMPOUNDS SUITABLE FOR NUCLEATING POLYLACTIC ACID POLYMER

CROSS REFERENCE TO RELATED APPLICATIONS

This application is a national stage filing under 35 U.S.C. 371 of PCT/US2016/037361, filed Jun. 14, 2016, which claims the benefit of U.S. Provisional Application No. 62/182,821, filed Jun. 22, 2015, the disclosure of which is incorporated by reference in its/their entirety herein.

BACKGROUND

Lactic acid is a renewable material obtained by the bacterial fermentation of corn starch or cane sugar, and thus is considered a natural or in otherwords "biomass" material. Lactic acid has two optical isomers: L-lactic acid (also known as (S)-lactic acid) and D-lactic acid (also known as (R)-lactic acid), depicted as follows:

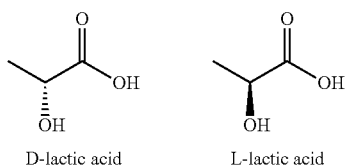

D-lactic acid    L-lactic acid

Polyesterification of lactic acid affords polylactic acid polymer.

More typically, lactic acid is typically converted to the cyclic lactide monomer, and the lactide undergoes ring opening polymerization, such as depicted as follows:

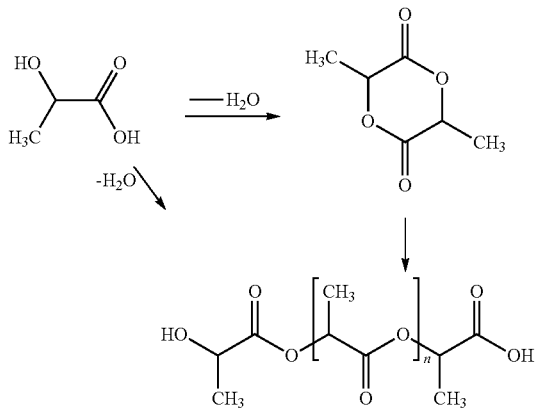

The resulting polymer material is typically referred to as polylactide polymer.

The degree of crystallinity, and hence many important properties, is largely controlled by the ratio of D and/or meso-lactide to L cyclic lactide monomer used. Likewise, for polymers prepared by direct polyesterification of lactic acid, the degree of crystallinity is largely controlled by the ratio of polymerized units derived from D-lactic acid to polymerized units derived from L-lactic acid.

A nucleating agent can be added to polylactide polymer to accelerate crystallization.

SUMMARY

In one embodiment a composition is described comprising a semicrystalline polylactic acid polymer; and a nucleating agent having the formula:

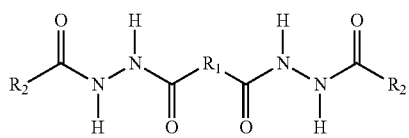

In some embodiments, $R_1$ is an alkylene group and $R_2$ is a $C_1$-$C_6$ alkyl group. In other embodiments, $R_1$ is a $C_{10}$-$C_{20}$ alkylene group; and $R_2$ is an alkyl group. In some embodiments, $R_2$ is an alkyl group having no greater than 5, 4, 3, 2, or 1 carbon atom.

In some embodiments, the semicrystalline polylactic acid polymer comprises at least 90 wt.-% of L-lactide and less than 10, 9, 8, 7, 6, 5, 4, 3, or 2 wt.-% of D-lactide and/or meso-lactide.

In other embodiments, articles such as a film or fiber are described comprising the semicrystalline polylactic acid polymer and a nucleating agent, as described herein.

In other embodiments, hydrazide compounds are described having the formula:

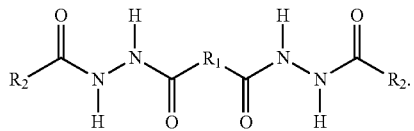

In some embodiments, $R_1$ is an alkylene group and $R_2$ is a $C_1$-$C_6$ alkyl group. In other embodiments, $R_1$ is a $C_{10}$-$C_{20}$ alkylene group; and $R_2$ is an alkyl group. In some embodiments, $R_2$ is an alkyl group having no greater than 5, 4, 3, 2, or 1 carbon atom.

DETAILED DESCRIPTION

Presently describes are hydrazide (e.g. dihydrazide) compounds suitable for use as a nucleating agent for a polylactic acid ("PLA") polymer.

The hydrazide compounds generally have the formula:

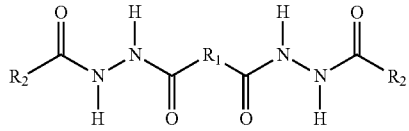

wherein $R_1$ is an alkylene group and $R_2$ is an alkyl group as described herein.

In some embodiments, the hydrazide compound are be prepared by reacting a hydrazide compound with a halogenated (e.g. chlorinated) aliphatic dicarboxylic acid compound.

Hydrazides are a class of organic compounds sharing a common functional group characterized by a nitrogen to nitrogen covalent bond with 4 substituents, at least one substituent being an acyl group. The general structure for a hydrazide is $R_2$—$CONR_3N$—$R_4R_5$. In the case of acetyl hydrazide, $R_2$ is methyl and $R_3$, $R_4$, and $R_5$ are hydrogen. In the case of octanoyl hydrazide, $R_2$ is an alkyl group having 7 carbon atoms and $R_3$, $R_4$, and $R_5$ are hydrogen.

In some embodiments, $R_2$ of the hydrazide starting compound and resulting hydrazide nucleating agent is a (e.g. linear or branched) $C_1$-$C_6$ alkyl group. In some embodiments, $R_2$ is an alkyl group having no greater than 5, 4, 3, 2, or 1 carbon atom. The alkyl group is typically linear.

The (e.g. chlorinated) halogenated aliphatic dicarboxylic acid compound that is reacted with the hydrazide starting compound typically has the general structure:

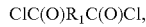

wherein $R_1$ is an alkylene.

The $R_1$ of the starting chlorinated aliphatic dicarboxylic acid compound and resulting hydrazide nucleating agent is generally a linear or branched $C_1$-$C_{20}$ alkylene. Thus, the $R_1$ can be characterized as a residue of a dicarboxylic acid. In typical embodiments, $R_1$ of the starting chlorinated aliphatic dicarboxylic acid compound and resulting hydrazide nucleating agent is a $C_{10}$-$C_{20}$ alkylene group. The alkylene group is typically linear. In some embodiments, $R_1$ of the starting chlorinated aliphatic dicarboxylic acid compound and resulting hydrazide nucleating agent is an alkylene group having no greater than 19, 18, 17, 16, 15, 14, 13, or 12 carbon atoms.

When utilized as a nucleating agent, the hydrazide compound is typically present at a concentration of at least 0.01, 0.05, 0.1, 0.2, 0.3, 0.5 or 0.5 wt.-% ranging up to about 1, 2, 3, 4 or 5 wt.-% based on the total weight polylactic acid ("PLA") polymer.

Without intending to be bound by theory, it has been found that as the chain length of $R_2$ decreases, the net melting endotherm (for the second heating scan, $\Delta H_{nm2}$) of a semicrystalline polylactic acid polymer composition containing such hydrazide compound as a nucleating agent increases. The net melting endotherm is the energy of the melting endotherm less the energy of the crystallization exotherm. The net melting endotherm of the compositions (i.e. taken from the microcompounder) is determined by the second heating scan. According to U.S. Pat. No. 6,005,068, a PLA film is considered to be amorphous if it exhibits a net melting endotherm of less than about 10 J/g. The net melting endotherm as well as other properties of the semicrystalline polylactic acid polymer composition comprising the hydrazide nucleating agent as described herein can be determined by Differential Scanning Calorimetry as further described in the forthcoming examples. In favored embodiments, $\Delta H_{nm2}$, of the semicrystalline polylactic acid polymer composition is greater than 10, 15, 20, 25, 30, 35, 40, or 45 J/g. The $\Delta H_{nm2}$, of the semicrystalline polylactic acid polymer composition typically does not exceed about 50 J/g.

In the absence of nucleating agent the polylactic acid ("PLA") polymer does not exhibit a first cooling scan crystallization peak temperature ($T_c$) for cooling rates ranging from 20° C./min to 50° C./min. However, by inclusion of a hydrazide nucleating agent as described herein, the polylactic acid ("PLA") polymer composition has a detectable first cooling scan crystallization peak temperature ($T_c$) for cooling rates ranging from 20° C./min to 50° C./min. Further, by inclusion of the nucleating agent, the polylactic acid ("PLA") polymer can exhibit a first cooling scan crystallization peak temperature ($T_c$) of at least 115° C. for cooling rates ranging from 2° C./min to 10° C./min. In some embodiments, the peak crystallization temperature is at least 120° C., 125° C., or 130° C. When the composition contains polylactic acid ("PLA") polymer and hydrazide nucleating agent as described herein, the peak crystallization temperature typically does not exceed about 135-140° C.

The crystallinity of a polylactic acid ("PLA") polymer composition can be determined according to the following equation:

Percent Crystallinity=$(\Delta H_{m2}-\Delta H_{cc2})/93.7\times100\%$.

In some embodiments, the polylactic acid ("PLA") polymer composition has a crystallinity of at least 10, 15, 20, 25, 30, 35, 40, 45, or 50%. When the composition contains of polylactic acid ("PLA") polymer and hydrazide nucleating agent as described herein, the crystallinity typically does not exceed about 55-60%.

The compositions described herein generally comprise a semicrystalline PLA polymer alone or in combination with an amorphous PLA polymer. Both the semicrystalline and amorphous PLA polymers generally comprise high concentrations of polymerized units derived from L-lactic acid (e.g. L-lactide) with low concentrations of polymerized units derived from D-lactic acid (e.g. D-lactide).

The semicrystalline PLA polymer typically comprises typically comprises at least 90, 91, 92, 93, 94, or 95 wt.-% of polymerized units derived from L-lactic acid (e.g. L-lactide) and no greater than 10, 9, 8, 7, 6, or 5 wt.-% of polymerized units derived from D-lactic acid and/or meso-lactide. In yet other embodiments, the semicrystalline PLA polymer comprises at least 96 wt.-% of polymerized units derived from L-lactic acid (e.g. L-lactide) and less than 4, 3, or 2 wt.-% of polymerized units derived from D-lactic acid (e.g. D-lactide and/or meso-lactide. Likewise the composition may comprise an even lower concentration of polymerized units derived from D-lactic acid (e.g. D-lactide and/or meso-lactide) depending on the concentration of semicrystalline PLA polymer in the composition. For example, if the composition comprises 50 wt.-% of a semicrystalline PLA having about 2 wt.-% D-lactide in combination with plasticizer and/or modifying polymer, the composition comprises about 0.1 wt.-% D-lactide. Suitable examples of semicrystalline PLA include Natureworks™ Ingeo™ 4042D and 4032D. These polymers have been described in the literature as having molecular weight Mw of about 200,000 g/mole; Mn of about 100,000 g/mole; and a polydispersity of about 2.0.

The composition may further comprise an amorphous PLA polymer blended with the semicrystalline PLA. The amorphous PLA typically comprises no more than 90 wt.-% of polymerized units derived from L-lactic acid and greater than 10 wt.-% of polymerized units derived from D lactic acid. In some embodiments, the amorphous PLA comprises at least 80 or 85 wt.-% of polymerized units derived from L-lactic acid (e.g. L-lactide). In some embodiments, the amorphous PLA comprises no greater than 20 or 15 wt.-%. of polymerized units derived from D-lactic acid. A suitable amorphous PLA includes Natureworks™ Ingeo™ 4060D grade. This polymer has been described in the literature as having a molecular weight Mw of about 180,000 g/mole.

In some embodiments, the PLA polymers have a melt flow rate (as measured according to ASTM D1238) of no greater than 25, 20, 15, or 10 g/min at 210° C. with a mass of 2.16 kg. In some embodiments, the PLA polymer has a melt flow rate of less than 10 or 9 g/min at 210° C. The melt flow rate is related to the molecular weight of the PLA polymer. The PLA polymer typically has a weight average molecular weight (Mw) as determined by Gel Permeation Chromatography with polystyrene standards of at least 50,000 g/mol; 75,000 g/mol; 100,000 g/mol; 125,000 g/mol;

150,000 g/mol. In some embodiments, the molecular weight (Mw) is no greater than 400,000 g/mol; 350,000 g/mol or 300,000 g/mol.

In some embodiments, the PLA polymers typically have a tensile strength ranging from about 25 to 150 MPa; a tensile modulus ranging from about 1000 to 7500 MPa; and a tensile elongation of at least 3, 4, or 5 ranging up to about 15%. In some embodiments, the tensile strength of the PLA polymer is at least 30, 40 or 50 MPa. In some embodiments, the tensile strength of the PLA polymer is no greater than 125, 100 or 75 MPa. In some embodiments, the tensile modulus of the PLA polymer is at least 1500, 2000, or 2500 MPa. In some embodiments, the tensile modulus of the PLA polymer is no greater than 7000, 6500, 6000, 5500, 5000, or 4000 MPa. Such tensile and elongation properties can be determined by ASTM D882 and are typically reported by the manufacturer or supplier of such PLA polymers.

In some embodiments, the PLA polymers are fiber-grade materials. Typical fiber properties include a tenacity of 2-7 grams/denier, an elongation of 10 to 70%, and a modulus of 25 to 70 grams/denier as measured by ASTM D2256/D3822.

The PLA polymers generally have a glass transition temperature, Tg, as can be determined by Differential Scanning Calorimetry (DSC) as described in the forthcoming examples, ranging from about 50 to 65° C.

The semicrystalline PLA polymers typically have a melting point ranging from 140 to 175° C. The PLA polymer, typically comprising a semicrystalline PLA alone or in combination with an amorphous PLA polymer can be melt-processed at temperatures of 180, 190, 200, 210, 220 or 230° C.

The composition typically comprises a semicrystalline PLA polymer or a blend of semicrystalline and amorphous PLA.

The composition may optionally further comprise a minor amount of a thermoplastic modifying polymer that is not a PLA polymer. In some embodiments the thermoplastic modifying polymer is a vinyl acetate polymer such as ethylene vinyl acetate copolymer.

The composition may optionally further comprises a plasticizer. The total amount of plasticizer in the composition typically ranges from about 5 wt-% to about 35, 40, 45 or 50 wt.-%, based on total weight of PLA polymer, polyvinyl acetate polymer, and plasticizer.

Various plasticizers that are capable of plasticizing PLA have been described in the art. The plasticizers are generally a liquid at 25° C. and typically have a molecular weight ranging from about 200 g/mol to 10,000 g/mol. In some embodiments, the molecular weight of the plasticizer is no greater than 5,000 g/mol. In other embodiments, the molecular weight of the plasticizer is no greater than 4,000, 3,000, 2,000 or 1,000 g/mol. Various combinations of plasticizers may be utilized.

The plasticizer preferably comprises one or more alkyl or aliphatic esters or ether groups. Multi-functional esters and/ or ethers are typically preferred. These include alkyl phosphate esters, dialkylether diesters, tricarboxylic esters, epoxidized oils and esters, polyesters, polyglycol diesters, alkyl alkylether diesters, aliphatic diesters, alkylether monoesters, citrate esters, dicarboxylic esters, vegetable oils and their derivatives, and esters of glycerine. Such plasticizers generally lack aromatic groups and halogen atoms and are anticipated to be biodegradable. Such plasticizers commonly further comprise linear or branched alkyl terminal group groups having a carbon chain length of $C_2$ to $C_{10}$.

In one embodiment, the plasticizer is a bio-based citrate-based plasticizer represented by the following Formula (I):

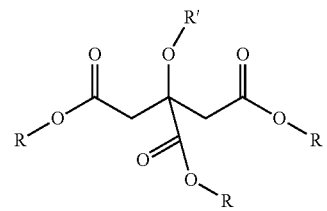

wherein
R is independently an alkyl group that may be the same or different; and
R' is an H or an ($C_1$ to $C_{10}$) acyl group.

R are typically independently linear or branched alkyl groups having a carbon chain length of $C_1$ to $C_{10}$. In some embodiments, R is a $C_2$ to $C_8$ or $C_2$ to $C_4$ linear alkyl group. In some embodiments, R' is acetyl. In other embodiments, at least one R is a branched alkyl groups having a carbon chain length of $C_5$ or greater. In some embodiments, the branched alkyl group has a carbon chain length no greater than 8.

Representative citrate-based plasticizer include for example triethyl citrate, acetyl triethyl citrate, tributyl citrate, acetyl tributyl citrate, trihexyl citrate, acetyl trihexyl citrate, trioctyl citrate, acetyl trioctyl citrate, butyryl trihexyl citrate, acetyl tris-3-methylbutyl citrate, acetyl tris-2-methylbutyl citrate, acetyl tris-2-ethylhexyl citrate, and acetyl tris-2-octyl citrate, In another embodiment, the plasticizer comprises a polyethylene glycol backbone and ester alkyl terminal groups. The molecular weight of the polyethylene glycol segment is typically at least 100, 150 or 200 g/mole and no greater than 1,000 g/mole. In some embodiments, the polyethylene glycol segment has a molecular weight no greater than 900, 800, 700, or 600 g/mole. Examples include polyethylene glycol (400) di-ethylhexonate available from Hallstar, Chicago, Ill. under the trade designation "TegMeR™ 809" and tetraethylene glycol di-ethylhexonate available from Hallstar, Chicago, Ill. under the trade designation "TegMeR™ 804".

Other known nucleating agents may optionally be present in the PLA composition. When other nucleating agents are present, the sum of the nucleating agents may be present in the concentration ranges previously described. Suitable nucleating agent(s) include for example inorganic minerals, organic compounds, salts of organic acids and imides, finely divided crystalline polymers with a melting point above the processing temperature of PLA, and combinations of two or more of the foregoing. Suitable nucleating agents typically have an average particle size of at least 25 nanometers, or at least 0.1 micron. Combinations of two or more different nucleating agents may also be used.

Examples of useful nucleating agents include, for example, talc (hydrated magnesium silicate—$H_2Mg_3(SiO_3)_4$ or $Mg_3Si_4O_{10}(OH)_2$), silica ($SiO_2$), titania ($TiO_2$), alumina ($Al_2O_3$), zinc oxide, sodium salt of saccharin, calcium silicate, sodium benzoate, calcium titanate, aromatic sulfonate derivative, boron nitride, copper phthalocyanine, phthalocyanine, sodium salt of saccharin, isotactic polypropylene, polybutylene terephthalate, as well as salts of a phosphorous-containing aromatic organic acid such as zinc phenylphosphonate, magnesium phenylphosphonate, disodium 4-tert-butylphenyl phosponate, and sodium diphenylphosphinates.

In some embodiments, the composition may further comprise inorganic fillers such as for the purpose of prevent blocking or sticking of layers or rolls of the film during storage and transport. Inorganic fillers include clays and minerals, either surface modified or not. Examples include talc, diatomaceous earth, silica, mica, kaolin, titanium dioxide, perlite, and wollastonite.

Organic biomaterial fillers include a variety of forest and agricultural products, either with or without modification. Examples include cellulose, wheat, starch, modified starch, chitin, chitosan, keratin, cellulosic materials derived from agricultural products, gluten, flour, and guar gum. The term "flour" concerns generally a composition having protein-containing and starch-containing fractions originating from one and the same vegetable source, wherein the protein-containing fraction and the starch-containing fraction have not been separated from one another. Typical proteins present in the flours are globulins, albumins, glutenins, secalins, prolamins, glutelins. In some embodiments, the composition comprises little or no organic biomaterial fillers such a flour. Thus, the concentration of organic biomaterial filler (e.g. flour) is less than 10, 9, 8, 7, 6, 5, 4, 3, 2, or 1 wt.-% of the total composition.

The composition and film may optionally contain one or more conventional additives. Additives include, for example, antioxidants, stabilizers, ultraviolet absorbers, lubricants, processing aids, antistatic agents, colorants, impact resistance aids, matting agents, flame retardants (e.g. zinc borate), pigments, and the like.

In preparing a composition as described herein, the PLA composition and nucleating agent, etc. are heated (e.g. 180-250° C.) and thoroughly mixed using any suitable means known by those of ordinary skill in the art. For example, the composition may be mixed by use of a (e.g., Brabender) mixer, extruder, kneader or the like.

Following mixing, the composition may be formed into a (e.g. cast) film using known film-forming techniques, taking in to consideration the scale of the process and available equipment. In some embodiments, the PLA composition is transferred to a press and then compressed and solidified to form individual sheets of PLA film. In other embodiments, the PLA composition may be extruded through a die onto a casting roll maintained at a suitable cooling temperature to form a continuous length of PLA film. In some embodiments, during the film extrusion, the casting roll temperature is maintained preferably at 80 to 120° C. to obtain crystallization of PLA films on the casting roll.

The PLA compositions described herein can be used in a variety of products including films, fibers (e.g. staple fiber, continuous filaments, nonwovens, textiles), injection molded articles, and 3-D printed articles.

When the film is a monolithic film, the thickness of the film is typically at least 10, 15, 20, or 25 microns (1 mil) to 500 microns (20 mils) thickness. In some embodiments, the thickness of the film is no greater than 400, 300, 200, 150 or 50 microns. The film may be in the form of individual sheets, particularly for a thickness of greater than 20 mils. The (e.g. thinner) film may be in the form of a roll-good.

When the film is a film layer of a multilayer film, the multilayer film typically has the thickness just described. However, the thickness of the film layer may be less than 10 microns. In one embodiment, the film layer comprising the composition described herein is an exterior layer or in other words a skin layer. A second film layer is disposed upon the skin layer. The second film layer typically has a different composition than the skin layer.

Fibers, such as those prepared from melt-blown processes can have a fiber diameter less than 10, 9, 8, 7, 6, or 5 micrometers. The fiber diameter is typically at least 1 or 2 microns. The basis weight of the (e.g. melt-blown) nonwoven web is typically at least 25, 30, 35, or 40 gsm and may range up to about 125 gsm. In some embodiments, the basis weight is less than 100, 90, 80, or 70 gsm. The solidity of the (e.g. melt-blown) nonwoven web may ranges from about 2 to 6, 7, 8, 9, or 10%.

The following Examples are set forth to describe additional features and embodiments of the invention. All parts are by weight unless otherwise indicated.

EXAMPLES

TABLE 1

| Materials | | |
|---|---|---|
| Trade Designation | Description | Source |
| Ingeo ™ Biopolymer 6100D ("6100D") | Polylactic acid, dried more than 24 hours at 71° C. before use. | NatureWorks LLC, Minnetonka, MN |
| Ingeo ™ Biopolymer 6202D | Polylactic acid, dried more than 24 hours at 71° C. before use. | NatureWorks LLC, Minnetonka, MN |
|  | Acetyl hydrazide | Alfa Aesar |
| DMA | N,N-Dimethylacetamide | Sigma-Aldrich |
|  | Dodecanedioyl chloride | Sigma-Aldrich |
|  | Octanoyl hydrazide | TCI America |
|  | Pyridine | Alfa Aesar |
| IRGACLEAR XT 386 | 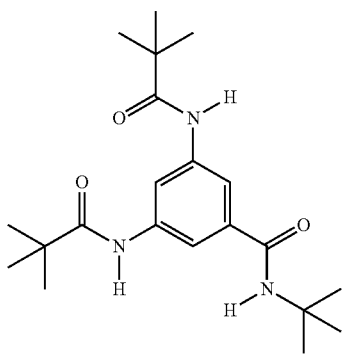 [SMILES: CC(C)(C)NC(=O)c1cc(NC(=O)C(C)(C)C)cc(NC(=O)C(C)(C)C)c1] | BASF |

Compounding of PLA

Samples with 6100D

Nucleating Agents were compounded into dried PLA using a Xplore® MC 15 MicroCompounder from Xplore Instruments BV, The Netherands. The extrusion and melt temperatures were 200° C. and 190° C., respectively. The materials were compounded for 1 minute with a screw speed of 100 rpm.

Samples with 6202D

These samples were extruded into a melt blown web at 290° C. with a twin-screw extruder. The nominal fiber properties were an effective fiber diameter of 8 micrometers, solidity of 5.5%, and a basis weight of 65 grams per square meter. The amount of nucleating agent is 1.0%.

Example 1: Preparation of Compound I

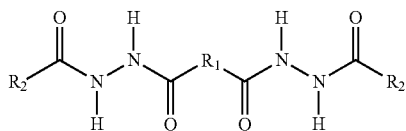

wherein $R_2$ is methyl and $R_1$ is a $C_{10}$ alkylene.

An oven-dried glass round-bottom flask (RBF) was charged with 51.4 grams of degassed DMA together with 3.04 grams of acetyl hydrazide (MW=74.08, mol=0.04) and 4.37 grams of pyridine (MW=79.10, mol=0.06). The mixture was stirred and cooled in an ice bath. 5.00 grams of dodecanedioyl dichloride (MW=267.20, mol=0.02) was added to the RBF via an addition funnel. The reaction turned cloudy and was allowed to reach room temperature and then stirred for 1 hour at 55° C. The mixture was poured into ~300 grams of deionized water, vacuum filtered with several water rinses and then dried in a vacuum oven. The amount of recovered material was 4.87 grams (76% yield).

The structure was confirmed by 1H NMR to be Compound I. The measured melting point for Compound I was 221° C.-224° C. The melting points for acetyl hydrazide and dodecanedioc acid were 58-68° C. and 127-129° C., respectively.

Example 2: Preparation of Compound II

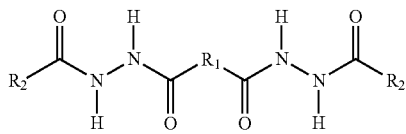

wherein $R_2$ is heptyl and $R_1$ is a $C_{10}$ alkylene.

The procedure was the same as in Example 1, except that octanoyl hydrazide was used in place of acetyl hydrazide, and the filtrate was washed with 0.1M NaOH, followed by a water/acetone mixture prior to vacuum drying. The amount of recovered material was 10.41 grams (95% yield) of a white powder. The melting point was measured and found to be 211-215° C. The melting point for octanoyl hydrazide was measured to be 88-89° C.

DSC—Differential Scanning Calorimetry

The glass transition temperature, crystallization temperature, melting temperature, etc. of each sample was measured using a Q2000 DIFFERENTIAL SCANNING CALORIMETER (TA Instruments), according to ASTM D3418-12. Each sample (4-8 mg) was heated from 0 to 200° C. at 10° C./min in a first heating scan and held for 1 minutes to erase its thermal history, then cooled to –0° C. at 20° C./min in a first cooling scan, and heated to 200° C. at 10° C./min in a second heating scan. The second heating scan was used to determine Tg of the compositions prepared from extrusion compounding or melt blown fiber web. Various parameters can be derived from the DSC as defined as follows:

$T_g$—refers to the midpoint temperature of the second heating scan, described as $T_{mg}$ in ASTM D3418-12.

$T_c$—refers to the crystallization peak temperature of the first cooling scan, described as $T_{pc}$ in ASTM D3418-12.

$T_{m1}$ and $T_{m2}$—refer to the melting peak temperature of the first and second heating scan, respectively, described as $T_{pm}$ in ASTM D3418-12.

The ability of the composition to crystallize was determined by calculating the net melting endotherm, $\Delta H_{nm2}$, associated with the crystalline material formed during the second cooling scan was calculated with the following equation, $$\Delta H_{nm2} = \Delta H_{m2} - \Delta H_{cc2}$$

where $\Delta H_{m2}$ is the melting endotherm mass normalized enthalpy of the second heating scan and $\Delta H_{cc2}$ is the crystallization exotherm mass normalized enthalpy of the second heating scan (as described in section 11 of ASTM D3418-12).

The absolute values of the enthalpies associated with the exotherms and endotherms (i.e. $\Delta H_{m2}$ and $\Delta H_{cc2}$ were used in the calculations.

The percent crystallinity was calculated as follows:

$$\text{Percent Crystallinity} = (\Delta H_{m2} - \Delta H_{cc2})/93.7 \times 100\%$$

TABLE 2

DSC Data

| Sample | Nucleating Agent/weight percent | PLA Resin/weight percent | $\Delta H_{nm2}$, J/gram | Percent crystallinity |
|---|---|---|---|---|
| Example 3 | Compound I/1.0% | 6202D/99.0% | 18.8 | 20% |
| Example 4 | Compound I/1.0% | 6100D/99.0% | 48.5 | 52% |
| Example 5 | Compound II/1.0% | 6100D/99.0% | 6.3 | 6.7% |
| Comparative Example A | IRGACLEAR XT 386*/1.0% | 6100D/99.0% | 11.5 | 12.5% |

In addition, a sequential cooling procedure was developed and applied to 6100D and 6100D with 1% Compound I using scan rates of 2 C/min, 5 C/min, 10 C/min, 20 C/min and 50 C°/min. The crystallization peak temperatures ($T_c$) of the first cooling scan for each scan rate were used to determine nucleation efficiency. Higher crystallization peak temperatures were achieved for 6100D with Compound I over 6100D (TABLE 3). At 20° C./min or higher scan rate, little or no crystallization was observed for 6100D without nucleating agent. Our developed nucleating agent can improve the processability and product property of polylactic acid.

TABLE 3

Crystallization Peak Temperatures of First Cooling Scan

| | Crystallization Peak Temperatures ($T_c$) ° C. | |
|---|---|---|
| Scan Rates | 6100D | 6100D + 1% Compound I |
| 2° C./min | 111.7 | 133.1 |
| 5° C./min | 102.2 | 121.3 |
| 10° C./min | 98.6 | 115.4 |
| 20° C./min | not detected | 109.7 |
| 50° C./min | not detected | 100.3 |

What is claimed:

1. A composition comprising:
semicrystalline polylactic acid polymer; and
a nucleating agent having the formula:

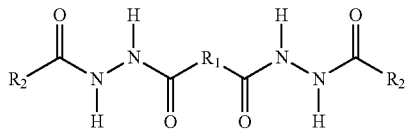

wherein $R_1$ is a $C_{10}$-$C_{20}$ alkylene group; and
$R_2$ is an alkyl group.

2. The composition of claim 1 wherein $R_2$ is linear.

3. The composition of claim 1 wherein the semicrystalline polylactic acid polymer comprises at least 90 wt.-% of L-lactide and less than 10 wt.-% of D-lactide and/or meso-lactide.

4. The composition of claim 1 wherein the semicrystalline polylactic acid polymer has a melt flow rate of no greater than 25 g/min at 210° C.

5. The composition of claim 1 wherein the semicrystalline polylactic acid polymer has a Tg ranging from about 50 to 65° C.

6. The composition of claim 1 wherein the composition has a second heating scan net melting endotherm ($\Delta H_{nm2}$) of greater than 10 J/g.

7. The composition of claim 1 wherein the composition has a detectable first cooling scan crystallization peak temperature ($T_c$) for cooling rates ranging from 20° C./min to 50° C./min.

8. The composition of claim 1 wherein the composition has a first cooling scan crystallization peak temperature ($T_c$) of at least 115° C. for cooling rates ranging from 2° C./min to 10° C./min.

9. The composition of claim 1 wherein $R_2$ is a $C_1$-$C_6$ alkyl group.

10. A film comprising the composition of claim 1.

11. A fiber comprising the composition of claim 1.

12. A hydrazide compound having the formula:

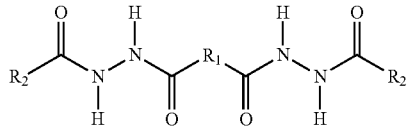

wherein $R_1$ is a $C_{10}$-$C_{20}$ alkylene group; and
$R_2$ is an alkyl group.

13. The hydrazide compound of claim 12 wherein $R_2$ is a $C_1$-$C_6$ alkyl group.

* * * * *

UNITED STATES PATENT AND TRADEMARK OFFICE
CERTIFICATE OF CORRECTION

| | |
|---|---|
| PATENT NO. | : 10,556,857 B2 |
| APPLICATION NO. | : 15/737473 |
| DATED | : February 11, 2020 |
| INVENTOR(S) | : Nathan Schultz et al. |

It is certified that error appears in the above-identified patent and that said Letters Patent is hereby corrected as shown below:

In the Specification

Column 1,
Line 19, delete "otherwords" and insert -- other words --, therefor.

Column 2,
Line 59, after "are" delete "be".

Column 4,
Line 22, after "polymer" delete "typically comprises".
Line 53, delete "wt.-%." and insert -- wt.-% --, therefor.

Column 6,
Line 29, delete "citrate," and insert -- citrate. --, therefor.
Line 64, delete "phosponate," and insert -- phosphonate, --, therefor.

Column 9,
Line 5, delete "Netherands." and insert -- Netherlands. --, therefor.
Line 40, delete "1H" and insert -- $^1$H --, therefor.
Line 43, delete "dodecanedioc" and insert -- dodecanedioic --, therefor.

Column 10,
Line 5, delete "-0° C." and insert -- 0° C. --, therefor.
Line 33, after "$\Delta H_{cc2}$" insert -- ) --.
Line 58, delete "2 C/min, 5 C/min, 10 C/min, 20 C/min" and insert -- 2° C./min, 5° C./min, 10° C./min, 20° C./min --, therefor.

Signed and Sealed this
Fifth Day of May, 2020

Andrei Iancu
*Director of the United States Patent and Trademark Office*